US006203803B1

(12) United States Patent
De La Charriere et al.

(10) Patent No.: US 6,203,803 B1
(45) Date of Patent: *Mar. 20, 2001

(54) USE OF A SUBSTANCE P ANTAGONIST IN A COSMETIC COMPOSITION, AND THE COMPOSITION THUS OBTAINED

(75) Inventors: Olivier De La Charriere, Paris; Lionel Breton, Versailles, both of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/881,272

(22) Filed: Jun. 24, 1997

Related U.S. Application Data

(63) Continuation of application No. 08/358,562, filed on Dec. 14, 1994, now abandoned.

(51) Int. Cl.$^7$ ...................................................... A61K 7/00
(52) U.S. Cl. ............................ 424/401; 424/59; 424/62; 424/63; 424/69; 424/70.1; 424/78.02; 424/43; 424/DIG. 1; 514/844; 514/845; 514/846; 514/847; 514/848; 514/880; 514/937; 514/974
(58) Field of Search .............................. 424/401, 59, 62, 424/63, 69–70.1, 78.02, 43–45, DIG. 1; 514/844–848, 880, 937–944, 974

(56) References Cited

U.S. PATENT DOCUMENTS

| | | |
|---|---|---|
| 3,266,934 | 8/1966 | Reiss et al. . |
| 4,477,439 | 10/1984 | D'Alelio . |
| 4,943,432 | 7/1990 | Biener . |
| 5,047,409 | 9/1991 | Di Schiena et al. . |
| 5,079,010 | 1/1992 | Natterer . |
| 5,593,992 | 1/1997 | Adams et al. . |
| 5,658,581 | * 8/1997 | de Lacharrieve ................ 424/401 |
| 5,679,360 | * 10/1997 | de Lacharriere ................ 424/401 |
| 5,714,155 | * 2/1998 | de Lacharriere ................ 424/401 |
| 5,716,625 | 2/1998 | Hahn et al. . |

FOREIGN PATENT DOCUMENTS

| | | |
|---|---|---|
| 3320539 A1 | 12/1983 | (DE) . |
| 3338957 | 5/1985 | (DE) . |
| 3627746 A1 | 2/1988 | (DE) . |
| 0280692 | 7/1990 | (DE) . |
| 0297062 | 1/1992 | (DE) . |
| 0217975 | 4/1987 | (EP) . |
| 0 299 457 A2 | 1/1989 | (EP) . |
| 0 360 390 | 3/1990 | (EP) . |
| 0 401 503 | 4/1990 | (EP) . |
| 0 429 366 A1 | 5/1991 | (EP) . |
| 0439640 | 8/1991 | (EP) . |
| 0 461 526 A2 | 12/1991 | (EP) . |
| 0459890 | 12/1991 | (EP) . |
| 0 522 808 | 7/1992 | (EP) . |
| 0 514 273 A1 | 11/1992 | (EP) . |
| 0 520 555A1 | 12/1992 | (EP) . |
| 0 522 808 A2 | 1/1993 | (EP) . |
| 0 545 478 A1 | 6/1993 | (EP) . |
| 0586929 | 3/1994 | (EP) . |
| 0 612 525 A1 | 8/1994 | (EP) . |
| 0 668 075 A2 | 8/1995 | (EP) . |
| 5.394 | 10/1967 | (FR) . |
| 2184890 | 6/1978 | (FR) . |
| 0 528 495 A1 | 2/1993 | (FR) . |
| 2271774 | 4/1994 | (GB) . |
| WO 83/01252 | 4/1983 | (WO) . |
| WO87/01935 | 10/1986 | (WO) . |
| WO 90/05729 | 5/1990 | (WO) . |
| WO 91/18899 | 12/1991 | (WO) . |
| WO93/01165 | 7/1992 | (WO) . |
| WO 93/01159 | 1/1993 | (WO) . |
| WO 93/01160 | 1/1993 | (WO) . |
| WO 93/01169 | 1/1993 | (WO) . |
| WO 93/01170 | 1/1993 | (WO) . |
| WO 93/04040 | 3/1993 | (WO) . |
| WO 93/14084 | 7/1993 | (WO) . |
| WO 96/19181 | 6/1996 | (WO) . |
| WO 96/19182 | 6/1996 | (WO) . |
| WO 96/19183 | 6/1996 | (WO) . |
| WO 96/19184 | 6/1996 | (WO) . |
| WO 96/19228 | 6/1996 | (WO) . |
| WO 97/15276 | 5/1997 | (WO) . |

OTHER PUBLICATIONS

Foreman, Int. Archs Allergy appl. Immun. 82: 366–371 (1987).
Watling et al., Neurotransmissions, vol. VIII, No. 3, Sep. 1992.
Sakurada et al., Brain Research, 593 (1992), 319–322.
Wallengren, British Journal of Dermatology (1991) 124: 324–328.
Wallengren et al., Contact Dermatitis 1988, 19: 351–354.
Moussaoui et al., Br. J. Pharmacol. (1993), 109: 259–264.
Lotti et al., J. Am. Acad. Dermatol. 1994, 30: 232–235.
Eedy, Brit J. Dermat. (1993) 128, S.597–605.
Lowe III, DN&P (1992) 5(4), S. 223–228.
English abstract of DE 3320539 A.
Rajadhyaksha, *Chemical Abstracts*, vol. 107, 1987, #223281.*
Pi Schiena, *Chemical Abstracts*, vol. 106, 1987, #107768.*
Smith et al., *Chemical Abstracts*, vol. 114, 1991, #206554.*
Dufetel et al., *Chemical Abstracts*, vol. 116, 1992, #135998.*
Maison G. deNavarre, *The Chemistry and Manufacture of Cosmetics*, 2nd Ed. vol. IV, p. 1261 (1975).
Alexander A. Fisher, "Irritant Reactions from Topical Urea Preparations Used for Dry Skin Advantages of a Urea–Free 'Dead Sea Salt' Cream", *Current Contact News*, vol. 18, pp. 761–772 (1976).

(List continued on next page.)

Primary Examiner—Gollamudi S. Kishore
(74) Attorney, Agent, or Firm—Burns, Doane, Swecker & Mathis, L.L.P.

(57) ABSTRACT

The invention concerns the use of a substance P antagonist in a cosmetic composition used to treat sensitive skin. More specifically, the invention relates to a substance P antagonist used to prevent and/or combat skin irritations, desquamation, erythemas, sensations of dysesthesia/overheating, or pruritus of the skin.

44 Claims, No Drawings

OTHER PUBLICATIONS

*The United States Pharmacopeia*, "Alumina/Drug Substances and Dosage Form", pp. 20 and 22 (1975).
*Nordia Briefs*, "A Salt–Containing Cream for Dry Skin", No. 484, Jan. 1978.
*Cosmetic Counter*, vol. 109, Oct. 1994.
Jancso–Gabor, "Action of rare earth metal complexes on neurogenic as well as on bradykinin–induced inflammation", *J. Pharm. Pharmac.*, 22:366–371 (1970).
"La peau sensible, un authentique syndrome clinique", *Le Quotidien du Medecin*, No. 5747, Dec. 6, 1995; Cosmetologie, *Therapeutique*, No. 1511, Dec. 17, 1995.
Uy Dong Sohn et al, "Agonist–Independent, Muscle–Type–Specific Signal Transduction Pathways in Cat Esophageal and Lower Esophageal Sphincter Circular Smooth Muscle", *J. of Pharmacology & Experimental Therapeutics*, 273:481–491 (1995).
Mitsuo Ishizawa, "Contractile Responses of Longitudinal Muscle Strip to 5–HT and Influences of Divalent Cations in the Guinea–Pig Isolated Colon", *J. Smooth Muscle Res.*, 30:65–72 (1994).
H. Goodman, *Cosmetic Dermatology*, First Edition, Fourth Impression, p. 181 (1936).
*Martindale*, The Extra Pharmacopoeia, Twenty–seventh Edition, The Pharmaceutical Press, London, pp. 219, 1775 and 1814 (1977).
*McGraw–Hill Dictionary of Scientific and Technical Terms*, Fifth Edition, pp. 109 and 332.

Sohn et al, Different Receptors Activate a Different Single G–Protein in Esophageal. (Gis) and in LES (Gq) Circular Smooth Muscle, *Gastroenterology*, vol. 104 (1993).
Sohn et al, "Different Receptors Activate a Different Single G–Protein in Esophageal (Gi3) and in LES (Fa) Circular Smooth Muscle", Rhode Island Hospital and Brown University, *Gastroenterology*, vol. 109, p. A586 (Apr. 1993).
S.M. Moussaoui et al, *Br. J. Pharmacol.*, "A non–peptide $NK_1$–receptor antagonist, RP 67580, inhibits neurogenic inflammation postsynaptically", vol. 109, No. 1, 1993, pp. 259–265.
J. Wallengren, *Br. J. Dermatol.*, "Substance P antagonist inhibits immediate and delayed type cutaneous hypersensitivity reactions", vol. 124, No. 4, 1991, pp. 324–328.
J. Wallengren et al, *Contact Dermatitis*, "Some neuropeptides as modulators of experimental contact allergy", vol. 19, No. 5, 1988, pp. 351–354.
T. Lotti et al, *J. Am. Acad. Dermatol.*, "Treatment of aquagenic pruritus with topical capsaicin cream", vol. 30, No. 2PT1, Feb. 1994, pp. 232–235.
T. Sakurada et al, *Brain Res.*, "A selective and extremely potent antagonist of the neurokinin–1 receptor", vol. 593, No. 2, 1992, pp. 319–322.
K. Folkers et al, *Proc. Natl. Acad. Sci. USA*, "Spantide II, an effective tachykinin antagonist having high potency", vol. 87, No. 12, 1990, pp. 4833–4855.

* cited by examiner

USE OF A SUBSTANCE P ANTAGONIST IN A COSMETIC COMPOSITION, AND THE COMPOSITION THUS OBTAINED

This application is a continuation of application Ser. No. 08/358,562, filed Dec. 14. 1994 now abandoned.

The present invention concerns the use of a substance P antagonist in a cosmetic composition used to treat sensitive skin, and the cosmetic composition obtained.

It is known that some skin is more sensitive than others. Until now, the symptoms of sensitive skin were poorly characterized, and, accordingly, the problem of sensitive skin was poorly defined. No one knew exactly what process was implicated in skin sensitivity. Some specialists thought that sensitive skin reacted to cosmetic products, while others felt sensitive skin reacted to a number of external factors not necessarily associated with cosmetics.

A number of tests were conducted to attempt to identify sensitive skin. For example, these tests made use of lactic acid and DMSO, which are known irritants. (See, for example, the article by K. Lammintausta et al., *Dermatoses,* 1988, 36, pages 45–49, and the article by T. Agner and J. Serup, *Clinical and Experimental Dermatology,* 1989, 14, pages 214–217.) However, these tests did not make it possible to characterize sensitive skin.

In addition, sensitive skin was held to resemble allergic skin.

Because the characteristics features of sensitive skin were poorly known, treatment has proved very difficult until now. Skin was treated indirectly, for example, by restricting the use of irritating products such as surfactants, preservatives, and perfumes in cosmetic compounds.

The Applicant conducted numerous clinical tests and was able to determine the symptoms shown in sensitive skin. These symptoms are, in particular, subjective in nature, i.e., basically sensations of dysesthesia. These are more or less painful sensations in a skin area, e.g., tingling, prickling, itching or pruritus, burning, overheating, discomfort, tugging sensations, etc.

The Applicant was also able to show that sensitive skin was not allergic skin. Indeed, allergic skin reacts to an external agent, i.e., an allergen, which triggers an allergic reaction. This is an immunological process which occurs only when an allergen is present and which does not affect sensitized subjects. In the Applicant's view, the basic feature of sensitive skin is, on the contrary, a response mechanism to external factors which may affect any individual, even though individuals considered to have sensitive skin react faster than others. This mechanism is not immunological, but aspecific.

The Applicant has since discovered that sensitive skin could be divided into two major clinical groups, irritable and/or reactive skin, and intolerant skin.

An irritable and/or reactive skin reacts by means of pruritus, that is, by itching or tingling, to various factors such as the environment, emotion, food, wind, friction, shaving, soap, surfactants, hard water having a high limestone concentration, temperature variations, or wool. In general, these signs are associated with dry skin with or without desquamation, or with skin exhibiting erythema.

Intolerant skin reacts by producing sensations of overheating, tugging, prickling, and/or redness to various factors such as the environment, emotion, and food. In general, these signs are associated with skin exhibiting hyperseborrhea or acne, with or without desquamation, and with erythema.

"Sensitive" scalp has a more pathognomonic clinical semiology: the sensations of pruritus and/or tingling or overheating are triggered basically by localized factors, such as rubbing, soap, surfactants, hard water containing a high limestone concentration, shampoos or lotions. These sensations are sometimes triggered by factors such as the environment, emotion, and/or food. Erythema and hyperseborrhea of the scalp, as well as the presence and extent of dandruff, are frequently associated with the aforementioned signs.

Furthermore, in some anatomical regions such as the major bend areas (the inguinal, genital, axillary, popliteal, and submammary regions and the bend of the elbow) and the feet, sensitive skin leads to pruriginous and/or sensations of dysesthesia (overheating, tingling) linked, in particular, to sweat, rubbing, wool, surfactants, hard water containing high limestone concentrations, and/or to temperature variations.

To determine whether a particular skin is sensitive or not, the Applicant also perfected a test. In fact, after conducting a large number of tests for the purpose of defining sensitive skin, the Applicant found, surprisingly, that there was link between persons having sensitive skin and those who reacted to a topical application of capsaicin.

The capsaicin test is performed by applying, over approximately 4 $cm^2$ of skin, 0.05 ml of a cream containing capsaicin in a concentration of 0.075% and by noting the appearance of subjective signs caused by this application, such as tingling, burning, and itching. In subjects with sensitive skin, these signs appear at between 3 and 20 minutes following application, and are followed by the appearance of an erythema, which begins at the periphery of the area of application.

To date, capsaicin has been used as a drug, in particular to treat the pain arising from shingles. Capsaicin causes the release of neuropeptides, in particular tachykinins, which emanate from nerve ends in the epidermis and dermis. The Applicant found that the physiopathological process common to all states of sensitive skin was linked to a pronounced ability to release tachykinins, and, more specifically of substance P, in the skin. The manifestations of dysesthesia caused by their release are termed "neurogenic."

Substance P is a chemical polypeptide produced and released by nerve endings. It belongs to the group of tachykinins. Substance P acts in particular in pain transmission and in diseases of the central nervous system, such as anxiety and schizophrenia, in respiratory, inflammatory, gastrointestinal, and rheumatic diseases, and in certain skin disorders, such as eczema.

The Applicant has now discovered that the basic characteristic of sensitive skin is linked to the release of substance P, and thus, that the use of substance P antagonists could produce a preventive and/or curative effect on sensitive skin.

To treat sensitive skin, the Applicant thus contemplated the use of substance P antagonists. Indeed, the Applicant found, surprisingly, that the incorporation of a substance P antagonist in a cosmetic compound made it possible to prevent irritation, sensations of dysesthesia, and pruritis in the skin.

Therefore, the present invention concerns the use of a substance P antagonist in a composition containing a cosmetically-acceptable medium in order to treat sensitive skin.

The present invention further relates to the use of a substance P antagonist to prevent and/or combat skin irritations, desquamation, erythemas, sensations of overheating or of dysesthesia, and/or pruritis in the skin.

A cosmetically-acceptable medium is a medium compatible with the skin, the nails, and the hair. The composition containing the substance P antagonist may be applied on the face, the neck, the hair, and the nails, or any other cutaneous region of the body.

To be acknowledged as a substance P antagonist, a substance must possess the following characteristics:
a selective affinity for the NK1 receptors on the tachykinins;
a pharmacological substance P-antagonist action; that is, it must induce a consistent pharmacological response in at least one of the following two tests:
the antagonist substance must reduce the extravasation of plasma through the vascular wall caused by the capsaicin or by antidromic nerve excitation, or else
the antagonist substance must cause inhibition of the contraction of the smooth muscles caused by administration of substance P.

To date, substance P antagonists have been used to treat the diseases indicated above. To this end, reference may be made to the following documents; U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569, GB-A-2216529, EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116, EP-A-522808, and WO-A-93/01165.

To date, no one had established a link between substance P and sensitive skin. The clinical signs of sensitive skin are basically subjective: tingling, pricking, pruritis, tugging, and overheating, and they are sometimes associated with erythema. These signs are produced by aspecific external factors. The symptoms are essentially localized on the face, the neck, and the scalp, but may also appear over the entire body.

The substance P antagonist according to the invention may be a peptide or a nitrogenous non-peptide derivative, and, more specifically, a compound comprising a nitrogenous heterocyclic compound or an atom of nitrogen bonded directly or indirectly to a benzene ring.

In accordance with the invention, use may be made, of example, of sendide or spantide II as a substance P antagonist peptide.

Sendide corresponds to the formula:

wherein:
Tyr is tyrosine
D-Phe is D-phenylalanine,
Phe is phenylalanine,
D-His is D-histidine,
Leu is leucine, and
Met is methionine.

Spantide II corresponds to the formula:

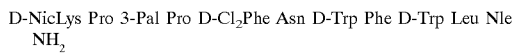

wherein:
D-NicLys is D-lysine nicotinate,
Pro is proline
3-Pal is 3-pyridylalanine,
D-Cl₂Phe is D-dichlorophenylalanine,
Asn is asparagin,
D-Trp is D-tryptophan,
Phe is phenylalanine,
Leu is leucine, and
Nle is nor-leucine.

According to the invention, the substance P antagonist peptide may also include the peptides described in the following documents: U.S. Pat. No. 4,472,305, U.S. Pat. No. 4839465, EP-A-101929, EP-A-333174, EP-A-336230, EP-A-394989, EP-A-443132, EP-A-498069, EP-A-515681, EP-A-517589, WO-A-92/22569, and GB-A-2216529.

Non-peptide substance P antagonists that can be used according to the invention include, in particular, compounds containing an atom of nitrogen bonded directly or indirectly to a benzene ring or contained in a heterocyclic compound.

As heterocyclic compound, use may be made according to the invention of those heterocyclic compounds described in the following documents: EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, and WO-A-93/09116. In particular, the compound containing at least one nitrogenous heterocyclic compound is a derivative of 2-tricyclyl-2-aminoethane, a derivative of spirolactame, a derivative of quinuclidine, an azacyclic derivative, a derivative of aminopyrrolidine, a derivative of piperidine, an aminoazaheterocyclic compound, or a derivative of isoindole.

As regards compounds containing a nitrogen atom bonded directly or indirectly to a benzene nucleus, mention may be made of those described in the following documents: EP-A-522808 and WO-A- 93/01165.

In the compositions according to the invention, the substance P antagonist is preferably used in a quantity ranging from 0.000001 to 5% by weight of the total weight of the composition, and, in particular, in a quantity ranging from 0.0001 to 0.1% by weight of the total weight of the composition.

The compositions according to the invention may be present in all galenical forms normally used for topical application, in particular solutions or dispersions of the lotion or serum type, liquid or semi-liquid milk emulsions produced by dispersion of a fatty phase in an aqueous phase (H/E) or the reverse (E/H), or cream- or gel-type emulsions having a soft consistency, or microgranulates or vesicular ionic and/or non-ionic dispersions. These compositions are prepared according to conventional practice.

They may also be used for hair, in the form of alcoholic or hydroalcoholic aqueous solutions or as creams, gels, emulsions, or foams, or again, as aerosol compositions also containing a pressurized propulsive agent.

The quantities of the various constituents in the compositions according to the invention are those conventionally used in the fields of study under consideration.

These compositions make up, in particular, creams for cleansing, protecting, treating, or caring for the face, the hands, the feet, the major anatomical bending areas, or for the body (e.g., day and night creams, make-up removal creams, foundation creams, and sunscreens), liquid foundations, make-up removal lotions, protective or skin-care body lotions, sunscreen lotions, skin-care lotions, gels, or foams, such as cleansing, sunscreen, and artificial tanning lotions, bath preparations, deodorant compositions containing a bactericide, after-shave gels or lotions, depilatory creams, and compositions used for insect stings and against pain.

The compositions according to the invention may also consist of solid preparations used for soaps and cleansing bars.

In addition, these compositions can be packaged as aerosol compositions also containing a pressurized propulsive agent.

The substance P antagonist may also be incorporated into various hair-care compositions, in particular shampoos, setting lotions, treatment lotions, hair creams or gels, coloring compositions (in particular oxidation dyes) potentially in the form of coloring shampoos, restructuring lotions for the hair, permanent compositions (in particular compositions for the first stage of a permanent), anti-hair loss lotions and gels, etc.

The cosmetic compositions according to the invention may also be used by mouth, e.g., in toothpastes. In this case, the compositions can contain conventional additives for compositions taken by mouth, in particular surfactants, thickeners, wetting agents, polishing agents such as silica, various active ingredients such as fluorides, in particular sodium fluoride, and potentially, sweeteners such as sodium saccharinate.

When the composition according to the invention is an emulsion, the proportion of the fatty phase may range from 5% to 80% by weight, and preferably from 5% to 50% by weight of the total weight of the composition. The oils, emulsifiers, and coemulsifiers used in the emulsion are chosen among those conventionally used in the cosmetic field. The emulsifier and coemulsifier are present in the composition in a proportion of between 0.3% and 30% by weight, and preferably between 0.5% and 30% by weight of the total weight of the composition. Moreover, the emulsion may contain lipidic vesicles.

In conventional fashion, the cosmetic composition according to the invention may also contain additives customarily used in cosmetics, such as water-absorbent or lipophilic gelling agents, water-absorbent or lipophilic active ingredients, preservatives, antioxidants, solvents, perfumes, fillers, screens, and coloring substances. The quantities of these various additives are those conventionally used in cosmetics; for example, from 0.01% to 10% of the total weight of the composition. These additives may, depending on the nature thereof, be added to the fatty phase, the aqueous phase, and/or in lipidic spherules.

As regards the oils that can be used according to the invention, mention may be made of mineral oils (vaseline oil), vegetable oils (liquid fraction of karite nut butter, sunflower oil), animal oils (perhydrosqualene), synthetic oils (Purcellin oil), silicone-containing oils (cyclomethicone), and fluorinated oils (perfluoropolyethers). Fatty alcohols and fatty acids (stearic acid) can be added to these oils.

Emulsifiers usable according to the invention include, for example, glycerol stearate, polysorbate 60, and the PEG-6/PEG-32/glycol stearate mixture sold under the trade name Tefose® 63 by the Gattefosse Company.

Solvents usable according to the invention include the lower alcohols, in particular ethanol and isopropanol.

As regards the water-absorbent gelling agents, mention may be made of carboxyvinyl polymers (carbomer), acrylic copolymers such as acrylate/alkylacrylate copolymers, polyacrylamides, polysaccharides such as hydroxylpropylcellulose, natural gums, and clays; and, as regards lipophilic gelling agents, modified clays such as bentonites and the metallic salts of fatty acids, such as aluminum stearates and hydrophobic silica.

The water-absorbent active ingredients include proteins and protein hydrolyzates, amino acids, polyalcohols, urea, allantoin, sugars and sugar derivatives, vitamins, and hydroxy acids.

The lipophilic active ingredients include retinol (vitamin A) and the derivatives thereof, tocopherol (vitamin E) and the derivatives thereof, essential fatty acids, ceramides, essential oils, and salicylic acid and the derivatives thereof.

Substance P antagonists may be combined, among other products, with active ingredients intended, in particular, for the prevention and/or treatment of skin disorders.

These active ingredients include, for example:

agents modulating the differentiation, proliferation, and/or skin pigmentation, such as retinoic acid and the isomers thereof, retinol and the esters thereof, vitamin D and the derivatives thereof, estrogens such as estradiol, kojik acid and hydroquinone;

antibacterial agents such as clindamycin phosphate, erythromycin, antibiotics belonging to the group of tetracyclines;

antiparasitic agents, in particular metronidazole, crotamiton, and pyrethrinoids;

antifungal agents, in particular the compounds belonging to the imidazoles, such as econazole, ketoconazole, or miconazole and the salts thereof, the polyene compounds, such as amphotericin B, compounds belonging to the group of allylamines, such as terbinafine and octopirox;

anti-inflammatory steroid agents, such as hydrocortisone, betamethasone valerate, clobetasol propionate, or non-steroid anti-inflammatory agents such as ibuprofen and the salts thereof, diclofenac and the salts thereof, acetylsalicylic acid, acetaminophen, and glycyrrhetinic acid;

anesthetic agents, such as lidocaine chlorhydrate and the derivatives thereof;

anti-pruriginous agents, such as thenaldine, trimeprazine, and cyproheptadine;

antiviral agents, such as acyclovir;

keratolytic agents, such as alpha- and beta-hydroxycarboxylic and beta-ketocarboxylic acids, the salts, amides, and esters thereof, and, more especially, hydroxy acids, such as glycolic, lactic, salicylic, and citric acid, and, in general fruit acids, and n-octanoyl-5-salicylic acid;

anti-free radical agents, such as alpha-tocopherol and the esters thereof, superoxide dismutases, some chelating agents of metals, and ascorbic acid and the esters thereof;

anti-seborrhea agents, such as progesterone;

anti-dandruff products, such as octopirox and zinc pyrithione;

acne-fighting products, such as retinoic acid or benzoyl peroxide.

Substance P antagonists are advantageously combined with active ingredients producing irritant side effects and widely used in the cosmetics field. The presence of an antagonist in a cosmetic composition containing an active ingredient producing an irritant effect makes it possible to attenuate, and indeed to eliminate, this irritant effect.

Accordingly, the invention also concerns a composition containing a cosmetically-acceptable medium and at least one active ingredient producing an irritant side effect, characterized by the fact that it contains a substance P antagonist.

In particular, the active ingredients exhibiting irritant side effects are chosen from among the α-hydroxy acids, the β-hydroxy acids, the α-ketonic acids, the β-ketonic acids, retinoids, anthralines, anthranoids, peroxides, minoxidil, lithium salts, antimetabolites, and vitamin D and the derivatives thereof.

The present invention further relates to a cosmetic treatment process characterized by the fact that a composition such as that described above and containing at least one substance P antagonist in a cosmetically-acceptable medium is applied on the skin, hair, and/or the mucous membranes.

The cosmetic treatment process according to the invention can be implemented, in particular, by applying hygienic or cosmetic compositions such as those specified above, in accordance with method of use normal for these compositions. For example: the application of creams, gels, serums, lotions, make-up removal lotions or sunscreen compositions on the skin or on dry hair, application of a hair lotion on wet hair, shampoos, or application of toothpaste on the gums.

The invention also concerns the use of capsaicin for preparing a composition intended to identify sensitive skin, and a process for identifying sensitive skin, which consists in applying a composition containing capsaicin on the skin.

The following examples illustrate the invention. In these examples, the proportion indicated are ponderal proportions.

EXAMPLE 1
Make-up Removal Face Lotion

| | |
|---|---|
| Spantide II | 5.00 |
| Antioxidant | 0.05 |
| Isopropanol | 40.00 |
| Preservative | 0.30 |
| Water | qsp 100% |

EXAMPLE 2
Make-up Removal Face Lotion

| | |
|---|---|
| Sendide | 0.0001 |
| Antioxidant | 0.05 |
| Isopropanol | 40.00 |
| Preservative | 0.30 |
| Water | qsp 100% |

EXAMPLE 3
Facial Care Gel

| | |
|---|---|
| Spantide II | 0.05 |
| Hydroxypropylcellulose (Klucel H, sold by the Hercules Company) | 1.00 |
| Antioxidant | 0.05 |
| Isopropanol | 40.00 |
| Preservative | 0.30 |
| Water | qsp 100% |

EXAMPLE 4
Facial Care Gel

| | |
|---|---|
| Sendide | 0.04 |
| Hydroxypropylcellulose (Klucel H, sold by the Hercules Company) | 1.00 |
| Antioxidant | 0.05 |
| Isopropanol | 40.00 |
| Preservative | 0.30 |
| Water | qsp 100% |

EXAMPLE 5
Facial Care Cream (oil-in-water emulsion)

| | |
|---|---|
| Spantide | 0.02 |
| Glycerol stearate | 2.00 |
| Polysorbate 60 (Tween 60 sold by the ICI Company) | 1.00 |
| Stearic acid | 1.40 |
| Triethanolamine | 0.70 |
| Carbomer | 0.40 |
| Liquid fraction of karite nut butter | 12.00 |
| Perhydrosqualene | 12.00 |
| Antioxidant | 0.05 |
| Perfume | 0.5 |
| Preservative | 0.30 |
| Water | qsp 100% |

EXAMPLE 6
Shampoo

| | |
|---|---|
| Spantide II | 0.02 |
| Hydroxypropylcellulose (Klucel H, sold by the Hercules Company) | 1.00 |
| Perfume | 0.50 |
| Preservative | 0.30 |
| Water | qsp 100% |

EXAMPLE 7
Anti-Wrinkle Facial Cream (oil-in-water emulsion)

| | |
|---|---|
| Sendide | 0.15 |
| Glycerol stearate | 2.00 |
| Polysorbate 60 (Tween 60, sold by the ICI Company) | 1.00 |
| Stearic acid | 1.40 |
| n-octanoyl-5-salicylic acid | 0.50 |
| Triethanolamine | 0.70 |
| Carbomer | 0.40 |
| Liquid fraction of karite nut butter | 12.00 |
| Perhydrosqualene | 12.00 |
| Antioxidant | 0.05 |
| Perfume | 0.50 |
| Preservative | 0.30 |
| Water | qsp 100% |

EXAMPLE 8
Shampoo

| | |
|---|---|
| Sendide | 0.003 |
| Hydroxypropylcellulose (Klucel H, sold by the Hercules Company) | 1.00 |
| Perfume | 0.50 |
| Preservative | 0.30 |
| Water | qsp 100% |

EXAMPLE 9
Emulsified Gel To Fight Insect Stings (oil-in-water emulsion)

| | |
|---|---|
| Cyclomethicone | 3.00 |
| Purcellin oil (sold by the Dragocco Company) | 7.00 |
| PEG-6/PEG-32/Glycerol Stearate (Tefose$^R$ sold by Gattefosse) | 0.30 |
| Spantide II | 0.02 |
| Preservative | 0.30 |
| Perfume | 0.40 |
| Carbomer | 0.60 |
| Crotamiton | 5.00 |
| Glycyrrhetinic acid | 2.00 |
| Ethyl alcohol | 5.00 |
| Triethanolamine | 0.20 |
| Water | qsp 100% |

EXAMPLE 10
Pain-Fighting Gel

| | |
|---|---|
| Spantide II | 0.03 |
| Hydroxypropylcellulose (Klucel H, sold by the Hercules Company) | 1.00 |
| Antioxidant | 0.05 |
| Lidocaine chlorhydrate | 2.00 |
| Isopropanol | 40.00 |
| Preservative | 0.30 |
| Water | qsp 100% |

EXAMPLE 11
Anti-Acne Rosacea Face Cream (oil-in-water emulsion)

| | |
|---|---|
| Spantide II | 0.25 |
| Glycerol stearate | 2.00 |
| Polysorbate 60 (Tween 60, sold by the ICI Company) | 1.00 |
| Stearic acid | 1.40 |
| Metronidazole | 1.00 |
| Triethanolamine | 0.70 |
| Carbomer | 0.40 |
| Liquid fraction of karite nut butter | 12.00 |
| Vaseline oil | 12.00 |
| Antioxidant | 0.05 |
| Perfume | 0.50 |
| Preservative | 0.30 |
| Water | qsp 100% |

EXAMPLE 12
Anti-Solar Erythema Cream (oil-in-water emulsion)

| | |
|---|---|
| Spantide II | 0.25 |
| Glycerol stearate | 2.00 |
| Polysorbate 60 (Tween 60, sold by the ICI Company) | 1.00 |
| Stearic acid | 1.40 |
| Glycyrrhetinic acid | 2.00 |
| Triethanolamine | 0.70 |
| Carbomer | 0.40 |
| Liquid fraction of karite nut butter | 12.00 |
| Sunflower oil | 10.00 |
| Antioxidant | 0.05 |
| Perfume | 0.50 |
| Preservative | 0.30 |
| Water | qsp 100% |

What is claimed is:

1. A topically applicable cosmetic composition which is adapted for use in a cosmetic regimen that comprises topical application of said composition to at least one of the skin, hair, or mucous membranes, which composition comprises:
   (1) an amount of at least one irritant substance sufficient to elicit an irritant side effect to a user having capsaicin-sensitive skin when utilized in a topical cosmetic regimen that does not include the use of a substance P antagonist, wherein said irritant substance is an active agent in said topical cosmetic regimen;
   (2) an amount of at least one substance P antagonist sufficient to prevent or alleviate said irritation when said composition is utilized in a topical cosmetic regimen on a user having capsaicin-sensitive skin, wherein said substance P antagonist is a substance which possesses at least one of the following characteristics:
      (i) it elicits a pharmacological response in at least one of the following tests:
         (a) it reduces the extravasation of plasma through the vascular wall caused by capsaicin or antidromic nerve excitation; and
         (b) it inhibits the contraction of smooth muscle induced by substance P; and
   (3) a cosmetically acceptable medium.

2. A topically applicable cosmetic composition which is adapted for use in a cosmetic regimen that comprises topical application of said composition to at least one of the skin, hair, or mucous membranes, which composition comprises:
   (1) an amount of at least one irritant substance sufficient to elicit an irritant side effect to a user having capsaicin-sensitive skin when utilized in a topical cosmetic regimen that does not include the use of a substance P antagonist, wherein said irritant substance is an active agent in said topical cosmetic regimen;
   (2) an amount of at least one substance P antagonist sufficient to prevent or alleviate said irritation when said composition is utilized in a topical cosmetic regimen on a user having capsaicin-sensitive skin, wherein said substance P antagonist is a substance which possesses at least one of the following characteristics:
      (i) it exhibits a selective affinity for the $NK_1$ receptors on the tachykinins; and
      (ii) it elicits a pharmacological response in at least one of the following tests:
         (a) it reduces the extravasation of plasma through the vascular wall caused by capsaicin or antidromic nerve excitation; and
         (b) it inhibits the contraction of smooth muscle induced by substance P; and
   (3) a cosmetically acceptable medium;
   wherein said topically applicable cosmetic composition comprises a galenic formulation selected from the group consisting of a solution or dispersion of the lotion or serum type, microgranulate dispersion, vesicular ionic or non-ionic dispersion, alcoholic or hydroalcoholic aqueous solution, cream, gel, emulsion of the oil-in-water or water-in-oil type, foam, aerosol, solid, and paste.

3. A topically applicable cosmetic composition which is adapted for use in a cosmetic regimen that comprises topical —continued

| | |
|---|---|
| Antioxidant | 0.05 |
| Perfume | 0.50 |
| Preservative | 0.30 |
| Water | qsp 100% | application of said composition to at least one of the skin, hair, or mucous membranes, which composition comprises:

(1) an amount of at least one irritant substance sufficient to elicit an irritant side effect to a user having capsaicin-sensitive skin when utilized in a topical cosmetic regimen that does not include the use of a substance P antagonist, and wherein said irritant substance is an active agent in said topical cosmetic regimen;

(2) an amount of at least one substance P antagonist sufficient to prevent or alleviate said irritation when said composition is utilized in a topical cosmetic regimen on a user having capsaicin-sensitive skin, wherein said substance P antagonist is a substance which possesses at least one of the following characteristics:
  (i) it elicits a pharmacological response in at least one of the following tests:
    (a) it reduces the extravasation of plasma through the vascular wall caused by capsaicin or antidromic nerve excitation; and
    (b) it inhibits the contraction of smooth muscle induced by substance P; and (3) a cosmetically acceptable medium;

wherein said topically applicable cosmetic composition suitable for use in a cosmetic regimen is selected from the group consisting of a hair care composition, skin care composition, cleansing composition, sunscreen composition, and a mouth care composition.

4. A topically applicable cosmetic composition which is adapted for use in a cosmetic regimen that comprises topical application of said composition to at least one of the skin, hair, or mucous membranes, which composition comprises:

(1) an amount of at least one irritant substance sufficient to elicit an irritant side effect to a user having capsaicin-sensitive skin when utilized in a topical cosmetic regimen that does not include the use of a substance P antagonist, and wherein said irritant substance is an active agent in said topical cosmetic regimen;

(2) an amount of at least one substance P antagonist sufficient to prevent or alleviate said irritation when said composition is utilized in a topical cosmetic regimen on a user having capsaicin-sensitive skin, wherein said substance P antagonist is a substance which possesses at least one of the following characteristics:
  (i) it exhibits a selective affinity for the $NK_1$ receptors on the tachykinins; and
  (ii) it elicits a pharmacological response in at least one of the following tests:
    (a) it reduces the extravasation of plasma through the vascular wall caused by capsaicin or antidromic nerve excitation; and
    (b) it inhibits the contraction of smooth muscle induced by substance P; and (3) a cosmetically acceptable medium;

wherein said topically applicable cosmetic composition suitable for use in a cosmetic regimen is selected from the group consisting of a hair care composition, skin care composition, cleansing composition, sunscreen composition, and a mouth care composition.

5. A topically applicable cosmetic composition which is adapted for use in a cosmetic regimen that comprises topical application of said composition to at least one of the skin, hair, or mucous membranes, which composition comprises:

(1) an amount of at least one irritant substance sufficient to elicit an irritant side effect to a user having capsaicin-sensitive skin when utilized in a topical cosmetic regimen that does not include the use of a substance P antagonist, wherein said irritant substance is an active agent in said topical cosmetic regimen;

(2) an amount of at least one substance P antagonist sufficient to prevent or alleviate said irritation when said composition is utilized in a topical cosmetic regimen on a user having capsaicin sensitive skin, wherein said substance P antagonist is a substance which possesses at least one of the following characteristics:
  (i) it elicits a pharmacological response in at least one of the following tests:
    (a) it reduces the extravasation of plasma through the vascular wall caused by capsaicin or antidromic nerve excitation; and
    (b) it inhibits the contraction of smooth muscle induced by substance P; and (3) a cosmetically acceptable medium;

wherein said topically applicable cosmetic composition comprises a galenic formulation selected from the group consisting of a solution or dispersion of the lotion or serum type, microgranulate dispersion, vesicular ionic or non-ionic dispersion, alcoholic or hydroalcoholic aqueous solution, cream, gel, emulsion of the oil-in-water or water-in-oil type, foam, aerosol, solid, and paste.

6. A topically applicable cosmetic composition which is adapted for use in a cosmetic regimen that comprises topical application of said composition to at least one of the skin, hair, or mucous membranes, which composition comprises:

(1) an irritant substance which can elicit an irritant side effect to a user having capsaicin-sensitive skin when utilized in a topical cosmetic regimen, wherein said irritant substance is an active agent in said topical cosmetic regimen;

(2) at least one substance P antagonist wherein said substance P antagonist is a substance which possesses at least one of the following characteristics:
  (i) it elicits a pharmacological response in at least one of the following tests:
    (a) it reduces the extravasation of plasma through the vascular wall caused by capsaicin or antidromic nerve excitation; and
    (b) it inhibits the contraction of smooth muscle induced by substance P; and (3) a cosmetically acceptable medium.

7. The composition of claim 3, 4, wherein said hair care composition is selected from the group consisting of a shampoo, setting lotion, treatment lotion, hair cream, hair gel, coloring composition, restructuring lotion, permanent composition, anti-hair loss lotion, and anti-hair loss gel.

8. The composition of claim 3 or 4, wherein said hair care composition is in a galenic form selected from the group consisting of a cream, gel, emulsion, foam, and aerosol.

9. The composition of claim 3, 4, or 6, wherein said cosmetic composition is selected from the group consisting of a cleansing cream, skin protecting or skin treatment cream, make-up removal cream, foundation cream, sunscreen composition, liquid foundation, make-up removal lotion, protective or skin care lotion, skin care gel, skin care foam, bath preparation, deodorant composition, after-shave gel or lotion, depilatory cream, a composition for alleviating insect sting, a soap, and a cleansing bar.

10. The composition of claim 3 or 4, wherein said mouth care composition is a toothpaste.

11. The composition of claim 1, 2, 5 or 6, wherein the irritant substance is selected from the group consisting of an α-hydroxy acid, β-hydroxy acid, α-ketonic acid, β-ketonic acid, retinoid, anthranoid, peroxide, minoxidil, lithium salt, anti-metabolite, and vitamin D.

12. The composition of claim 3 or 4, wherein the irritant substance is selected from the group consisting of an α-hydroxy acid, β-hydroxy acid, α-ketonic acid, β-ketonic acid, retinoid, anthranoid, peroxide, minoxidil, lithium salt, anti-metabolite, and vitamin D.

13. The composition of claim 1, 2, 5 or 6, wherein the amount of the substance P antagonist ranges from 0.000001 to 5% by weight relative to the total weight of the cosmetic composition.

14. The composition of claim 3 or 4, wherein the amount of the substance P antagonist ranges from 0.000001 to 5% by weight relative to the total weight of the cosmetic composition.

15. The composition of claim 1, 2, 5, or 6, wherein the amount of the substance P antagonist ranges from 0.0001 to 0.1% by weight relative to the total weight of the cosmetic composition.

16. The composition of claim 3, or 4 wherein the amount of the substance P antagonist ranges from 0.0001 to 0.1% by weight relative to the total weight of the cosmetic composition.

17. The cosmetic composition of claim 12, which comprises an additive selected from the group consisting of a surfactant, thickener, wetting agent, polishing agent, a fluoride compound, and sodium sacchararinate.

18. The cosmetic composition of claim 1, 2, or 5, which is an emulsion.

19. The cosmetic composition of claim 3, 4, or 6, which is an emulsion.

20. The cosmetic composition of claim 14, wherein the proportion of a fatty phase in said emulsion ranges from 5% to 80% by weight relative to the total weight of the composition.

21. The cosmetic composition of claim 18 or 19, wherein the proportion of a fatty phase in said emulsion ranges from 5% to 80% by weight relative to the total weight of the composition.

22. The cosmetic composition of claim 14, which comprises an emulsifier and co-emulsifier.

23. The cosmetic composition of claim 18 or 19, which comprises an emulsifier and co-emulsifier.

24. The cosmetic composition of claim 18, wherein the proportion of said emulsifier and co-emulsifier ranges from 0.3 to 30% by weight relative to the total weight of the composition.

25. The cosmetic composition of claim 19, wherein the proportion of said emulsifier and co-emulsifier ranges from 0.3 to 30% by weight relative to the total weight of the composition.

26. The cosmetic composition of claim 20, wherein said proportion ranges from 0.5 to 30% by weight.

27. The cosmetic composition of claim 26, wherein said proportion ranges from 0.5 to 30% by weight.

28. The cosmetic composition of claim 1, 2, 5, or 6, which comprises at least one cosmetic additive selected from the group consisting of a water-absorbent or lipophilic gelling agent, water-absorbent or lipophilic active ingredient, preservative, anti-oxidant, solvent, perfume, filler, sunscreen, and coloring substance.

29. The cosmetic composition of claim 3 or 4, which comprises at least one cosmetic additive selected from the group consisting of a water-absorbent or lipophilic gelling agent, water-absorbent or lipophilic active ingredient, preservative, anti-oxidant, solvent, perfume, filler, sunscreen, and coloring substance.

30. The cosmetic composition of claim 1, 2, 5 or 6, which comprises at least one oil selected from the group consisting of a mineral oil, vegetable oil, synthetic oil, silicon-containing oil, and fluorinated oil.

31. The cosmetic composition of claim 9 or 4, which comprises at least one oil selected from the group consisting of a mineral oil, vegetable oil, synthetic oil, silicon-containing oil, and fluorinated oil.

32. The cosmetic composition or claim 1, 2, 5 or 6, which comprises at least one emulsifier selected from the group consisting of glycerol stearate, polysorbate, and a polyethylene glycol/glycol stearate mixture.

33. The cosmetic composition or claim 3 or 4, which comprises at least one emulsifier selected from the group consisting of glycerol stearate, polysorbate, and a polyethylene glycol/glycol stearate mixture.

34. The cosmetic composition of claim 1, 2, 5 or 6, which comprises at least one water-absorbent gelling agent selected from the group consisting of a carboxyvinyl polymer, acrylic copolymer, polyacrylamide, polysaccharide, natural gum, clay, modified clay, and a metallic salt of a fatty acid.

35. The cosmetic composition of claim 3 or 4, which comprises at least one water-absorbent gelling agent selected from the group consisting of a carboxyvinyl polymer, acrylic copolymer, polyacrylamid, polysaccharide, natural gum, clay, modified clay, and a metallic salt of a fatty acid.

36. The cosmetic composition of claim 1, 2, 5 or 6, which comprises at least one lipophilic active agent selected from the group consisting of a retinoid, tocopherol, essential fatty acid, ceramide, essential oil, and salicylic acid.

37. The cosmetic composition of claim 3 or 4, which comprises at least one lipophilic active agent selected from the group consisting of a retinoid, tocopherol, essential fatty acid, ceramide, essential oil, and salicylic acid.

38. The cosmetic composition of claim 1, 2, 5 or 6, which comprises at least one of the following: an agent that modulates at least one of cell differentiation, proliferation or pigmentation, retinoic acid or an isomer or ester thereof, vitamin D, estrogen, antibacterial agent, antiparasitic agent, antibiotic, antifungal agent, anti-inflammatory steroid, anesthetic, anti-pruriginous agent, antiviral agent, keratolytic agent, anti-free-radical agent, anti-seborrhea agent, anti-dandruff agent, and anti-acne agent.

39. The cosmetic composition of claim 3 or 4, which comprises at least one of the following: an agent that modulates at least one of cell differentiation, proliferation or pigmentation, retinoic acid or an isomer or ester thereof, vitamin D, estrogen, antibacterial agent, antiparasitic agent, antibiotic, antifungal agent, anti-inflammatory steroid, anesthetic, anti-pruriginous agent, antiviral agent, keratolytic agent, anti-free-radical agent, anti-seborrhea agent, anti-dandruff agent, and anti-acne agent.

40. The cosmetic composition of claim 1, 2, 5 or 6, wherein said substance P antagonist is selected from the group consisting of a peptide, nitrogen-containing non-peptide compound, and a nitrogen containing heterocyclic compound.

41. The cosmetic composition of claim 3 or 4, wherein said substance P antagonist is selected from the group consisting of a peptide, nitrogen-containing non-peptide compound, and a nitrogen containing heterocyclic compound.

42. The cosmetic composition according to any one of claims 1 through 5, or 6, wherein capsaicin-sensitive skin is skin that elicits at least one sensitive skin reaction when capsaicin is topically applied thereto.

43. The cosmetic composition of claim 42, wherein said at least one sensitive skin reaction is selected from the group consisting of tingling, erythema, burning and itching.

44. The cosmetic composition of claim 43, wherein said sensitive skin reaction appears about three to twenty minutes following capsaicin application.

* * * * *

UNITED STATES PATENT AND TRADEMARK OFFICE
CERTIFICATE OF CORRECTION

PATENT NO. : 6,203,803 B1
DATED : March 20, 2001
INVENTOR(S) : Olivier de Lacharrière et al.

It is certified that error appears in the above-identified patent and that said Letters Patent is hereby corrected as shown below:

<u>Title page,</u>
Item [75], Inventors, change "Olivier De La Charriere" to -- Olivier de Lacharrière --.

Signed and Sealed this

Ninth Day of April, 2002

*Attest:*

*Attesting Officer*

JAMES E. ROGAN
*Director of the United States Patent and Trademark Office*